(12) United States Patent
Singanamalli et al.

(10) Patent No.: US 11,602,331 B2
(45) Date of Patent: Mar. 14, 2023

(54) DELIVERY OF THERAPEUTIC NEUROMODULATION

(71) Applicant: General Electric Company, Schenectady, NY (US)

(72) Inventors: Asha Singanamalli, Glenville, NY (US); David Andrew Shoudy, Niskayuna, NY (US); Jeffrey Michael Ashe, Gloversville, NY (US); Christopher Michael Puleo, Niskayuna, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 125 days.

(21) Appl. No.: 16/567,996

(22) Filed: Sep. 11, 2019

(65) Prior Publication Data
US 2021/0068793 A1    Mar. 11, 2021

(51) Int. Cl.
*A61B 8/00* (2006.01)
*A61N 7/00* (2006.01)
(Continued)

(52) U.S. Cl.
CPC ............ *A61B 8/54* (2013.01); *A61B 5/7267* (2013.01); *A61B 8/085* (2013.01); *A61B 8/4461* (2013.01);
(Continued)

(58) Field of Classification Search
CPC ......... A61B 8/54; A61B 8/085; A61B 5/7267; A61B 8/4461; A61B 5/02007; A61B 5/0036; A61N 7/00; A61N 2007/0091; A61N 2007/0026; A61N 2007/0095; A61N 2007/0082; A61N 2007/0052
See application file for complete search history.

(56) References Cited

U.S. PATENT DOCUMENTS

| 8,235,902 B2 | 7/2012 | Chen et al. |
| 2010/0286518 A1 | 11/2010 | Lee et al. |

(Continued)

FOREIGN PATENT DOCUMENTS

| WO | 2009035627 A2 | 3/2009 |
| WO | 2017127902 A1 | 8/2017 |
| WO | 2018177280 A1 | 10/2018 |

OTHER PUBLICATIONS

PCT/US2020/049482; International Search Report and Written Opinion dated Dec. 16, 2020; 13 pages.
(Continued)

*Primary Examiner* — Joseph M Santos Rodriguez
*Assistant Examiner* — Kaitlyn E Sebastian
(74) *Attorney, Agent, or Firm* — Fletcher Yoder P.C.

(57) ABSTRACT

Embodiments of the present disclosure relate to techniques for neuromodulation delivery. Based on image data acquired from the subject, control parameters controlling energy application of neuromodulating energy may be dynamically changed during the course of the delivery to maintain desired characteristics of the neuromodulating energy. For example, the beam of the neuromodulating energy may be dynamically adjusted to account for movement of an organ during breathing. In another embodiment, a desired region of interest is identified within the subject based on a trained neural network and the acquired image data.

21 Claims, 12 Drawing Sheets

(51) Int. Cl.
*A61B 8/08* (2006.01)
*A61B 5/00* (2006.01)
(52) U.S. Cl.
CPC ........ *A61N 7/00* (2013.01); *A61N 2007/0026* (2013.01); *A61N 2007/0091* (2013.01)

(56) References Cited

U.S. PATENT DOCUMENTS

| | | | |
|---|---|---|---|
| 2011/0028799 A1* | 2/2011 | Hyde | A61B 5/0022 600/300 |
| 2013/0144165 A1 | 6/2013 | Ebbini et al. | |
| 2014/0058292 A1* | 2/2014 | Alford | A61N 7/00 601/2 |
| 2014/0316269 A1 | 10/2014 | Zhang et al. | |
| 2015/0196783 A1 | 7/2015 | Emery et al. | |
| 2015/0265366 A1 | 9/2015 | Andrews et al. | |
| 2016/0151593 A1* | 6/2016 | Rapoport | A61B 5/087 128/204.23 |
| 2018/0028841 A1 | 2/2018 | Konofagou et al. | |
| 2018/0190377 A1* | 7/2018 | Schneemann | G06K 9/00275 |
| 2018/0344286 A1 | 12/2018 | Mienkina et al. | |
| 2019/0065970 A1 | 2/2019 | Bonutti et al. | |
| 2019/0336108 A1* | 11/2019 | Hope Simpson | A61B 8/0891 |
| 2020/0046992 A1* | 2/2020 | Tracey | A61N 1/40 |
| 2020/0054228 A1* | 2/2020 | Puleo | A61B 5/6825 |
| 2020/0069976 A1* | 3/2020 | Puleo | A61B 90/96 |
| 2021/0145399 A1* | 5/2021 | Xie | A61B 8/5246 |

OTHER PUBLICATIONS

Gasper, Andrew J., et al.; "Real-Time Implementation of a Dual-Mode Ultrasound Array System: In Vivo Results", IEEE Transactions on Biomedical Engineering, vol. 60, Issue: 10, pp. 2751-2759, Oct. 2013.

* cited by examiner

Dose delivery controller

Prescription

Patient ID: ABC123DEF456
Device ID: 00001234ABCD
Prescription date: 01/08/2019: 04:33:50 PM
Expiration date: 01/08/2019: 04:38:50 PM
Dose amount (sec): 5
Dose interval (sec): 10
Doses prescribed: 3
Doses remaining: 3

Status

Current time: 01/08/2019: 04:34:35 PM
Last dose: N/A
Next dose ready: 01/08/2019: 04:33:50 PM
Status: Ready
Dose accumulation: 0.00

Control

Start dose
Stop dose

Kidney

FIG. 11

Dose delivery controller

Prescription

Patient ID: ABC123DEF456
Device ID: 00001234ABCD
Prescription date: 01/08/2019: 04:33:50 PM
Expiration date: 01/08/2019: 04:38:50 PM
Dose amount (sec): 5
Dose interval (sec): 10
Doses prescribed: 3
Doses remaining: 2

Status

Current time: 01/08/2019: 04:34:51 PM
Last dose: 01/08/2019: 04:34:50 PM
Next dose ready: 01/08/2019: 04:35:00 PM
Status: Complete
Dose accumulation: 5.00

Control

Start dose
Stop dose

Liver

FIG. 14

DELIVERY OF THERAPEUTIC NEUROMODULATION

BACKGROUND

The subject matter disclosed herein relates to identify, target and/or dose regions of interest in a subject via application of neuromodulating energy to cause targeted physiological outcomes. In particular, the disclosed techniques may be part of a personalized treatment protocol.

Neuromodulation has been used to treat a variety of clinical conditions. For example, electrical stimulation at various locations along the spinal cord has been used to treat chronic back pain. However, positioning electrodes at or near the target nerves is challenging. For example, such techniques may involve surgical placement of the electrodes that deliver the energy. In addition, specific tissue targeting via neuromodulation is challenging. Electrodes that are positioned at or near certain target nerves mediate neuromodulation by triggering an action potential in the nerve fibers, which in turn results in neurotransmitter release at a nerve synapse and synaptic communication with the next nerve. Such propagation may result in a relatively larger or more diffuse physiological effect than desired, as current implementation of implanted electrodes stimulate many nerves or axons at once. Because the neural pathways are complex and interconnected, a more selective and targeted modulated effect may be more clinically useful. However, the effectiveness of selective targeting specific neural may be dependent on accurate positioning of the energy application device. Accurate focusing of neuromodulating energy may vary based on individual patient anatomy. For example, certain patients may have variations in organ size or location relative to other patients based on their height, weight, age, gender, clinical condition, etc. Further, patients may also exhibit anatomical changes over time or that may complicate accuracy in energy delivery.

BRIEF DESCRIPTION

The disclosed embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a neuromodulation delivery system is provided. The system includes an energy application device configured to deliver neuromodulating energy to a region of interest in a subject. The system also includes a controller configured to receive image data of an internal tissue of the subject; identify the region of interest within the image data; control application of the neuromodulating energy via the energy application device to the identified region of interest to deliver a dose of the neuromodulating energy thereto; receive updated image data of the internal tissue of the subject before delivering the dose is complete; identify a change in a location of the region of interest in relation to the energy application device based on the updated image data; and adjust application of the neuromodulating energy via the energy application device based on the changed location of the region of interest to continue the delivering of the dose of the neuromodulating energy to treat the subject.

In another embodiment, a method of delivery of neuromodulating energy is provided. The method includes the steps of delivering energy to a region of interest of a subject using control parameters, wherein the energy is a portion of a total energy of an individual dose to be applied to the region of interest and wherein the energy is applied using an energy application device; acquiring image data from the subject while delivering the energy and before the total energy of the individual dose is applied, the image data being representative of an internal tissue comprising the region of interest; identifying a change in location of the region of interest relative to the energy application device based on the image data; adjusting one or more control parameters of the set of control parameters based on the change in location of the region of interest; and delivering additional energy to the region of interest using the adjusted control parameters to deliver another portion of the total energy of the individual dose using the energy application device.

In another embodiment, a neuromodulation delivery system is provided. The system includes an energy application device configured to deliver neuromodulating energy to a region of interest in a subject. The system also includes a controller configured to control the energy application device to acquire image data, the image data being representative of an internal tissue of the subject; identify the region of interest based on the image data using a neural network trained on image data of respective internal tissues of a population of subjects, the respective internal tissues being a same type of tissue as the internal tissue of the subject; control application of the neuromodulating energy via the energy application device to the identified region of interest to deliver a dose of the neuromodulating energy to treat the subject; acquire updated image data while delivering the dose; and dynamically change one or more control parameters controlling the application of the neuromodulating energy based on the updated image data.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 11 is an example graphical user interface of an autonomous neuromodulation delivery system according to embodiments of the disclosure;

FIG. 14 is an example graphical user interface of an autonomous neuromodulation delivery system after completion of delivery of neuromodulating energy to the region of interest according to embodiments of the disclosure.

DETAILED DESCRIPTION

Figure 1:
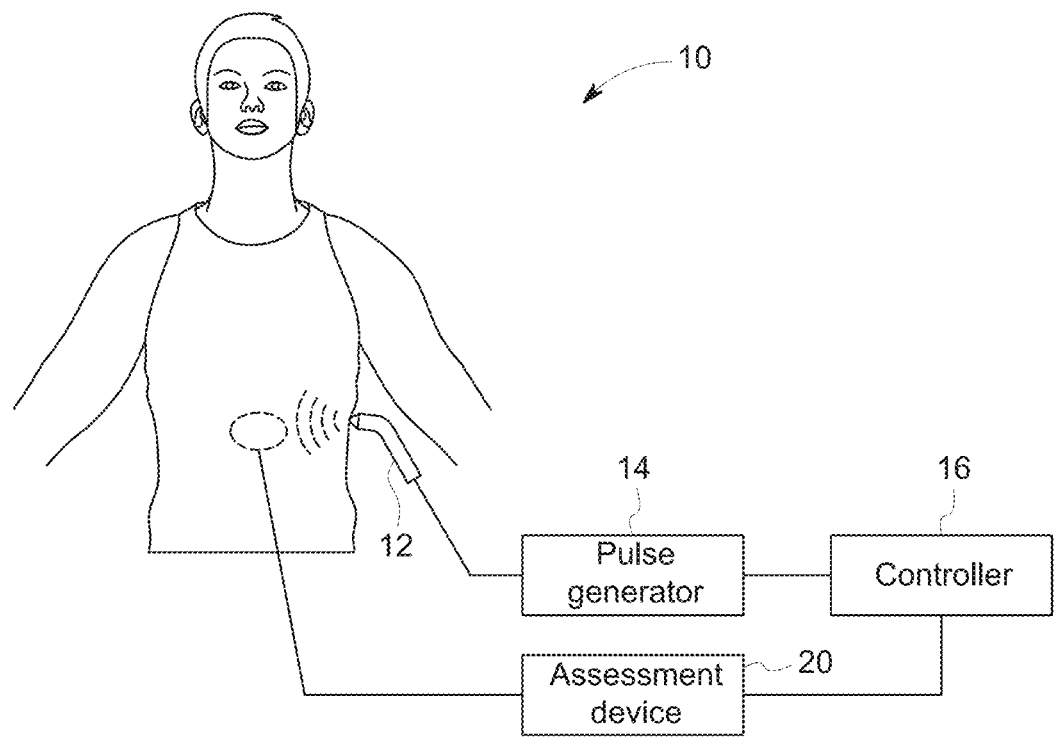
FIG. 1 is a schematic representation of an autonomous neuromodulation delivery system according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments," "in some embodiments," and "in one (an) embodiment."

Provided herein are techniques for neuromodulation of targeted regions of interest as part of a treatment protocol that permits reproducible and reliable application of energy to a particular region or regions of interest over the course of the treatment protocol. The disclosed techniques provide autonomous delivery of neuromodulating energy that accounts for and dynamically adjusts one or more parameters of the delivery based on changes in a location of a desired target of the energy (e.g., a region of interest) during the course of energy delivery such that the energy delivery need not be interrupted. For example, while patients may be instructed to remain still during delivery of neuromodulating energy, minor changes in patient position or even patient breathing may cause movement of internal organs within the body that may result in changes in a location of the target relative to an external or extracorporeal energy application device (e.g., an ultrasound therapy probe). Because neuromodulating energy can be focused on a volume of tissue that includes a particular axon terminal or a set of axon terminals within the tissue (and, conversely, that does not include other axon terminals present in the tissue), minor tissue movements may result in the focal zone of the energy application device being shifted away from the region of interest and to an adjacent area of the tissue that does not include the desired axon terminals and therefore, may not result in physiological outcomes associated with neuromodulation of the desired axon terminals. Movements of the region of interest even in the millimeter or centimeter range may result in inaccurate application of the neuromodulating energy and, in turn, may fail to achieve desired therapeutic goals.

To account for movements of the tissue over a time frame of application of a dose or multiple doses of neuromodulating energy, the delivery area may be expanded in volume outside of the region of interest to account for minor movements. However, such an approach may, depending on the particular region of interest, decrease a desired specificity of the treatment by exposing other axon terminals to neuromodulating energy, which may cause confounding physiological effects that may blunt or interfere with the desired therapeutic goals. Further, such an approach may also limit a total dose delivery at a single treatment session by exposing an overall larger volume of tissue to energy, thus reaching per-dose energy limits more rapidly and potentially before a desired dose to the region of interest is delivered.

The present techniques permit accurate delivery of neuromodulating energy that is user friendly and that removes or reduces anatomical guidance inputs by trained clinicians, thereby permitting at home or outpatient treatment by less experienced caregivers, which in turn expands treatment options. Further, while trained clinicians are capable of identifying anatomical landmarks to accurately guide energy delivery, each individual clinician may introduce their own preference biases to treatment, which may also interfere with accurate dose delivery over time, particularly if several clinicians are involved in care. The present techniques provide tools for inexperienced caregivers to deliver neuromodulating energy as part of a treatment protocol.

In one embodiment, the disclosed techniques incorporate imaging data acquired before and/or during a treatment session to track movements in a region of interest over time such that the energy can be refocused or redirected in real time to maintain energy delivery on or in the region of interest. The imaging data may be acquired using a multi-functional devices device that is configured to both acquire image data and deliver the neuromodulating energy. In one example, a neural network is used to identify an organ that includes a region, a region of interest, anatomical structures, or combinations thereof. Once identified, movement may be tracked based on the ongoing or updated acquired image data.

The neural network may be trained on images from a population of subjects such that the organ or other tissue including the region of interest may be quickly identified, in some embodiments without operator intervention. The neural network architecture may involve various layers that permit identification of structures based on morphology, pattern matching, edge identification, etc. The neural network may also be configured to identify the region of interest within the organ or tissue. For example, if the region of interest correspond to a porta hepatis region of a liver, the neural network may be trained, based on ground truth images of a population, to identify a region of interest that likely contains or overlaps the porta hepatis region in a particular subject.

To that end, the disclosed neuromodulation delivery techniques may be used in conjunction with a neuromodulation system configured to be used to deliver neuromodulating energy as part of a treatment protocol. FIG. 1 is a schematic representation of a system 10 for neuromodulation to achieve neuromodulating effects such as neurotransmitter release and/or activation of components (e.g., the presynaptic cell, the postsynaptic cell) of a synapse in response to an application of energy. The depicted system includes a pulse generator 14 coupled to an energy application device 12 (e.g., an ultrasound transducer). The energy application device 12 is configured to receive energy pulses, e.g., via leads or wireless connection, that in use are directed to a region of interest in an internal tissue or an organ of a subject, which in turn results in a targeted physiological outcome.

In certain embodiments, the energy application device 12 and/or the pulse generator 14 may communicate wirelessly, for example with a controller 16 that may in turn provide instructions to the pulse generator 14. In other embodiments, the energy application device 12 may be an extracorporeal device, e.g., may operate to apply energy transdermally or in a noninvasive manner from a position outside of a subject's body, and may, in certain embodiments, be integrated with the pulse generator 14 and/or the controller 16. In embodiments in which the energy application device 12 is extracorporeal, the energy application device 12 may be operated by a caregiver and positioned at a spot on or above a subject's skin such that the energy pulses are delivered transdermally to a desired internal tissue. Once positioned to apply energy pulses to the desired site, the system 10 may initiate neuromodulation of one or more nerve pathways to achieve targeted physiological outcome or clinical effects. In other embodiments, the pulse generator 14 and/or the energy application device 12 may be implanted at a biocompatible site (e.g., the abdomen) and may be coupled internally, e.g., via one or more leads. In some embodiments, the system 10 may be implemented such that some or all of the elements may communicate in a wired or wireless manner with one another.

In certain embodiments, the system 10 may include an assessment device 20 that is coupled to the controller 16 and that assesses characteristics that are indicative of whether the targeted physiological outcome of the modulation have been achieved. In one embodiment, the targeted physiological outcome may be local. For example, the modulation of one or more nerve pathways may result in local tissue or function changes, such as tissue structure changes, local change of concentration of certain molecules, tissue displacement, increased fluid movement, etc. The targeted physiological outcome may be a goal of the treatment protocol.

The modulation of one or more nerve pathways to achieve a targeted physiological outcome may result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 20 may be configured to assess concentration changes in some embodiments. In some embodiments, the assessment device 20 may be an imaging device configured to assess changes in organ size position, and/or tissue characteristics. In another embodiment, the assessment device 20 may be a circulating glucose monitor. While the depicted elements of the system 10 are shown separately, it should be understood that some or all of the elements may be combined with one another. In another embodiment, the assessment device may assess local temperature rises of the tissue, which may be detected using a separate temperature sensor or ultrasound imaging data from the energy application device 12 when configured for ultrasound energy application. Assessment of speed of sound differences may be detected through difference imaging techniques pre/during/post therapy.

Based on the assessment, the modulation parameters of the controller 16 may be altered such that an effective amount of energy is delivered. For example, if a desired modulation is associated with a change in concentration (circulating concentration or tissue concentration of one or more molecules) within a defined time window (e.g., 5 minutes, 30 minutes after a procedure of energy application starts) or relative to a baseline at the start of a procedure, a change of the modulation parameters such as pulse frequency or other parameters may be desired, which in turn may be provided to the controller 16, either by an operator or via an automatic feedback loop, for defining or adjusting the energy application parameters or modulation parameters of the pulse generator 14 until the modulation parameters result in an effective amount of energy being applied. As provided herein, the data of the assessment device 20 may be provided as part of a feedback loop to train a neural network for each individual as part of a treatment protocol and/or to redirect or refocus the energy to account for movement of the region of interest during treatment. In one embodiment, an initially defined region of interest may be refined to yield an updated region of interest based on feedback from the assessment device as to the efficacy of the neuromodulating energy over the course of the treatment protocol. The feedback may be, for example, changes in concentration of molecules of interest as a result of the application of neuromodulating energy. These refinements or updates to the region of interest may be used as part of patient-specific networks, where the network is updated to identify the specific region of interest that has the most impact on the physiological parameters of interest for that particular individual based on the desired clinical outcome.

The system 10 as provided herein may provide energy pulses according to various modulation parameters as part of a treatment protocol to apply the effective amount of energy. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. Further, the treatment protocol may specify a time of day to apply energy or a time relative to eating or other activity. The treatment duration to cause the targeted physiological outcomes may last for various time periods, including, but not limited to, from a few minutes to several hours. In certain embodiments, treatment duration with a specified stimulation pattern may last for one hour, repeated at, e.g., 72 hour intervals. In certain embodiments, energy may be delivered at a higher frequency, say every three hours, for shorter durations, for example, 30 minutes. The application of energy, in accordance with modulation parameters, such as the treatment duration, frequency, and amplitude, may be adjustably controlled to achieve a desired result.

Figure 2:
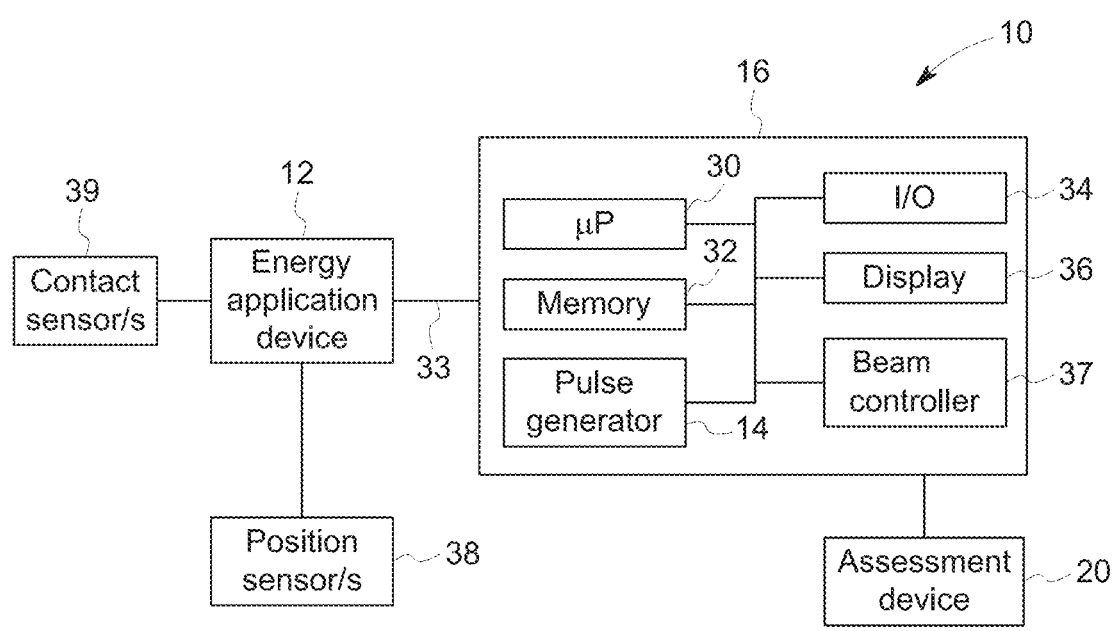
FIG. 2 is a block diagram of an autonomous neuromodulation delivery system according to embodiments of the disclosure.

FIG. 2 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 30 for controlling the device. Software code or instructions are stored in memory 32 of the controller 16 for execution by the processor 30 to control the various components of the device. The controller 16 and/or the pulse generator 14 may be connected to the energy application device 12 via one or more leads 33 or wirelessly. The processor 30 may be configured to access, from the memory 32, software to operate a neural network that has been trained previously on images of other subjects (e.g., that do not necessarily include the subject being treated). Further, the processor may be configured to permit updating of the neural network based on the image data of the subject of interest.

The controller 16 may include a user interface with input/output circuitry 34 and a display 36 that are adapted to allow a clinician to provide selection inputs or modulation parameters to modulation programs. However, certain embodiments of the system 10 may also include implementations without a display 36 that provide feedback using sounds or lights. For example, a relatively simple at-home system 10 may be configured with or without a display 36 and configured such that an inexperienced user is not provided with information that is unhelpful to achieving treatment goals. The processor 30 may be configured to operate a neural network and identify the region of interest using a relatively simple interface while providing guidance to move the energy application device 12 to a correct treatment position.

The system may include a beam controller 37 that may control a focus location of the energy beam of the energy application device 12 by controlling one or both of steering and/or focusing of the energy application device 12. The beam controller 37 may also control or one or more articulating portions of the energy application device 12 to reposition the transducer. The beam controller may receive instructions from the processor 30 to cause changes in focusing and/or steering of the energy beam. The system 10 may be responsive to position sensor/s 38 and/or contact sensor/s 39 that provide feedback on the energy application device 12. The beam controller 37 may include a motor to facilitate steering of one or more articulating portions of the energy application device 12. In one embodiment, the motor/s are internal to the probe housing and a fixed surface (lens of an ultrasound probe) contacts the body. The motors internally can move in 1 to 6 degrees of freedom, while the probe remains stationary on the body. In an additional or alternative embodiment, the probe is shaped more like a conventional imaging probe, is held by a motorized fixture, and is moved along the skin in up to 6 degrees of freedom in a similar manner to freehand scanning. Changing angles corresponds to 3 degrees of freedom, and corresponds to steering the beam in 3D space. Changing the position corresponds to the other 3 degrees of freedom, and is comprised of XY movement to slide along the surface of the body, or Z movement corresponds to adjusting the depth of focus or contact force. It is contemplated that the system 10 may include features to permit position, steering, and/or focus adjustments to facilitate the techniques disclosed herein.

Each modulation program stored in the memory 32 may include one or more sets of modulation parameters including pulse amplitude, pulse duration, pulse frequency, pulse repetition rate, etc. The pulse generator 14 modifies its internal parameters in response to the control signals from controller device 16 to vary the stimulation characteristics of energy pulses transmitted through lead 33 to a subject to whom the energy application device 12 is applied. Any suitable type of pulse generating circuitry may be employed, including but not limited to, constant current, constant voltage, multiple-independent current or voltage sources, etc. The energy applied is a function of the current amplitude and pulse duration. The controller 16 permits adjustably controlling the energy by changing the modulation parameters and/or initiating energy application at certain times or cancelling/suppressing energy application at certain times. In one embodiment, the adjustable control of the energy application device to apply energy is based on information about a concentration of one or more molecules in the subject (e.g., a circulating molecule). If the information is from the assessment device 20, a feedback loop may drive the adjustable control. For example, a diagnosis may be made based on circulating glucose concentration, as measured by the assessment device 20, in response to neuromodulation. When the concentration is above a predetermined threshold or range, the controller 16 may initiate a treatment protocol of energy application to a region of interest (e.g., liver) and with modulation parameters that are associated with a reduction in circulating glucose. The treatment protocol may use different modulation parameters than those used in the diagnosis protocol (e.g., higher energy levels, more frequent application).

In one embodiment, the memory 32 stores different operating modes that are selectable by the operator. For example, the stored operating modes may include separate models or neural networks for identifying a particular region of interest and executing a set of modulation parameters associated with a particular treatment site, such as regions of interest in the liver, pancreas, gastrointestinal tract, spleen. Each organ or site may be associated with a different model. Further, different sites may have different associated modulation parameters based on the depth of the relevant organ, the size of the region of interest, the desired physiological outcome, etc. Rather than having the operator manually input the modes, the controller 16 may be configured to execute the appropriate instruction based on the selection of a particular organ. In another embodiment, the memory 32 stores operating modes for different types of procedures. For example, activation may be associated with a different stimulating pressure or frequency range relative to those associated with depressing or blocking tissue function.

In a specific example, when the energy application device is an ultrasound transducer, the effective amount of energy may involve predetermined temporal average intensity applied to a region of interest. For example, the effective amount of energy may include a time-averaged power (temporal average intensity) and peak positive pressure in the range of 1 mW/cm2-30,000 mW/cm² (temporal average intensity) and 0.1 MPa to 7 MPa (peak pressure). In one example, the temporal average intensity is less than 35 mW/cm², less than 500 mW/cm², or less than 720 mW/cm² in the region of interest. In an example, the temporal average intensity is associated with levels less than those associated with thermal damage and ablation/cavitation. In another specific example, when the energy application device is a mechanical actuator, the amplitude of vibration is in the range of 0.1 to 10 mm. The selected frequencies may depend on the mode of energy application, e.g., ultrasound or mechanical actuator. The controller 16 may be capable of operating in a validating mode to acquire a predetermined treatment position and the predetermined treatment position may be implemented as part of a treatment operating mode that is configured to execute a treatment protocol when the energy application device 12 is positioned at the predetermined treatment position.

The system may also include an imaging device that facilitates focusing the energy application device 12. In one embodiment, the imaging device may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 32 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 12 may be focused (e.g., using the beam controller 37) to a focus location on the selected volume corresponding to the region of interest. It should be understood that the image data used to guide the focus location may be a volume or a plane. For example, the energy application device 12 may be configured to first operate in the validating mode to acquire the predetermined treatment position by capturing image data to be used for identifying the predetermined treatment position associated with capturing the region of interest. The validating mode energy is not at levels and/or applied with modulation parameters suitable for neuromodulating treatment. However, once the region of interest is identified, the controller 16 may then operate in a treatment mode according to the modulation parameters associated with achieving targeted physiological outcomes.

The controller 16 may also be configured to receive inputs related to the targeted physiological outcomes as an input to the selection of the modulation parameters. For example, when an imaging modality is used to assess a tissue characteristic, the controller 16 may be configured to receive a calculated index or parameter of the characteristic. Based on whether the index or parameter is above or below a predefined threshold, a diagnosis may be made, and an indication of the diagnosis may be provided (e.g., via a display). In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 (e.g., an ultrasound transducer) may operate under control of the controller 16 to a) acquire image data of a tissue that may be used to spatially select a region of interest within the target tissue b) apply the modulating energy to the region of interest and c) acquire image data to determine that the targeted physiological outcome has occurred (e.g., via displacement measurement). In such an embodiment, the imaging device, the assessment device 20 and the energy application device 12 may be the same device.

Figure 3:
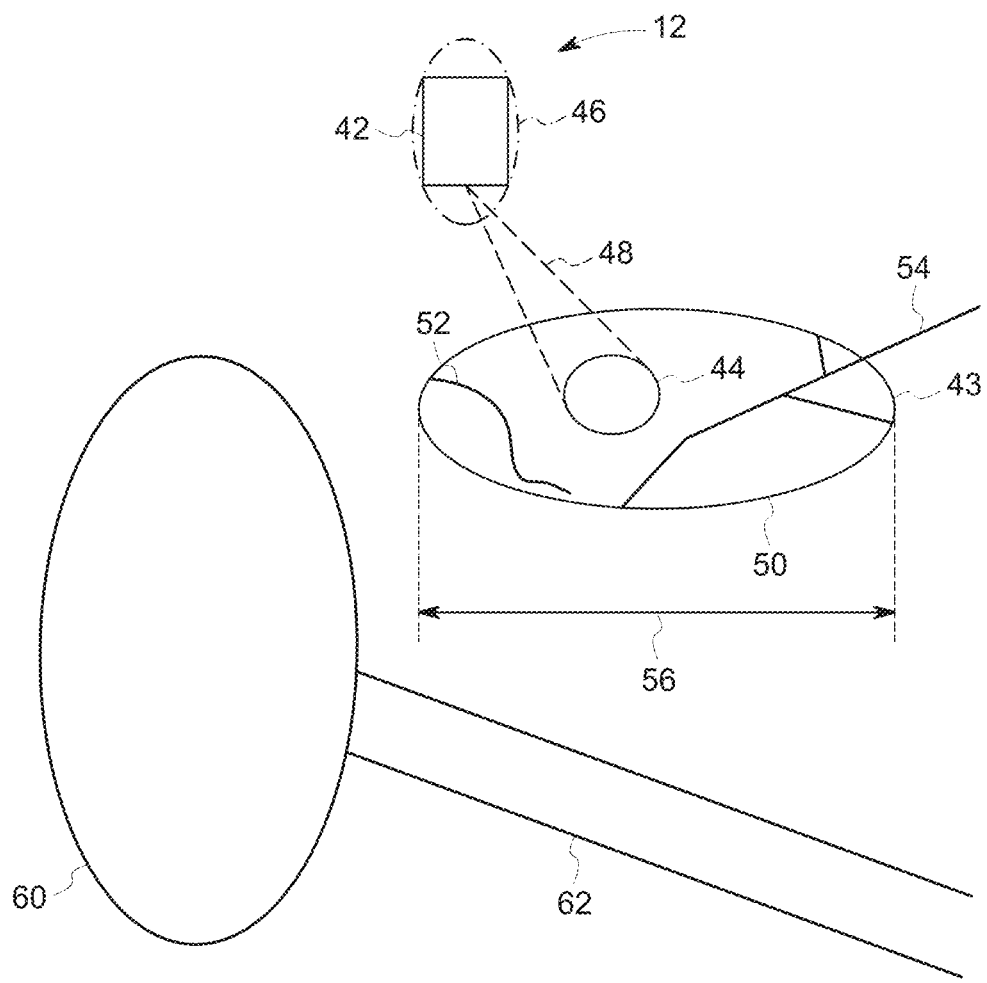
FIG. 3 is a schematic representation of an autonomous neuromodulation delivery system applying neuromodulating energy to a region of interest within a tissue including anatomical structures according to embodiments of the disclosure.

FIG. 3 shows energy delivery, using an energy application device 12 as provided, to a region of interest 44. The energy application device 12 includes an ultrasound transducer 42 (e.g., a transducer array) that is capable of applying energy to a target organ or tissue 43, e.g., a liver, a spleen, a pancreas. The energy application device 12 may include control circuitry for controlling the ultrasound transducer 42. The control circuitry of the processor 30 (FIG. 2) may be integral to the energy application device 12 (e.g., via an integrated controller 16) or may be a separate component. The energy application device 12 may also be configured to acquire image data to assist with spatially selecting a desired or targeted region of interest 44 and focusing the applied energy on the region of interest of the target tissue or structure.

The region of interest 44 and/or the target tissue 43 may include various anatomical features or structures to facilitate automatic identification, e.g., via a neural network, as provided herein. For example, the organ may have characteristic edges 50 in a particular shape, may have capillaries or smaller blood vessels 52 as well as internal nerve structures 54 that enter the tissue 43. The tissue 43 may be within a predictable size or volume range, based on subject size, weight, age, and/or clinical condition, or may feature dimension ranges 56, e.g., in the x, y, or z axis. The tissue 43 may be positioned relative to other internal structures, such as other organs 60 or larger blood vessels 62. These and other features may be provided as input to identification of the region of interest 44 and/or the target tissue 43. Further, these features may be acquired from patient populations to identify predictable characteristics (e.g., larger blood vessel locations, location of organs or glands) that tend to be stable across patient populations as well as more variable characteristics that vary between subjects and within a subject over time depending on clinical condition, metabolic state, patient weight, etc. For example, the size of certain organs may change after a meal. Other identifying features may be bifurcations in blood vessels, entry/exit points of arteries and veins into organs ("porta", "hilus", "hilum", "fissure", "indendation", "duct", etc.). Networks with different weights or filters may be used based on variability of these factors. As these factors change, the appropriate models trained specifically on other subjects with similar factors may be employed. One example may be the patient aging. Networks using different models may be available for individuals of different ages. As the patient's age changes, the most-appropriate model for the patient at a given time point may be selected. Accordingly, a suite of different networks may be accessible. Such networks may include more general or generic models, models for certain demographics, and fully individualized models.

The desired target tissue 43 may be an internal tissue or an organ that includes synapses of axon terminals and non-neuronal cells. The synapses may be stimulated by direct application of energy to the axon terminals within a field of focus or focal zone 48 of the ultrasound transducer 42 focused on a region of interest 44 of the target tissue 43 to cause action potentials and/or the release of molecules into the synaptic space, e.g., the release of neurotransmitters and/or the change in ion channel activity in turn causes downstream effects. The region of interest 44 may be selected to include a certain type of axon terminal, such as an axon terminal of a particular neuron type and/or one that forms a synapse with a certain type of non-neuronal cell. Accordingly, the region of interest 44 may be selected to correspond to a portion of the target tissue 43 with the desired axon terminals (and associated non-neuronal cells). The energy application may be selected to preferentially trigger a release of one or more molecules such as neurotransmitters from the nerve within the synapse or directly activate the non-neuronal cell itself through direct energy transduction (i.e. mechanotransduction or voltage-activated proteins within the non-neuronal cells), or cause an activation within both the neural and non-neuronal cells that elicits a desired physiological effect. The region of interest 44 may be selected as the site of nerve entry into the organ. In one embodiment, liver stimulation or modulation may refer to a modulation of the region of interest 44 at or adjacent to the porta hepatis. Identification of the predetermined treatment position 46 on the patient's skin (or garment) may include selection of the region of interest 44, whereby the position on the patient's body at which the region of interest 44 is within the focal zone 48 of the energy application device 12 when in operation is the predetermined treatment position 46.

The energy may be focused or substantially concentrated on a region of interest 44 and to only part of the internal tissue 43, e.g., less than about 50%, 25%, 10%, or 5% of the total volume of the tissue 43. That is, the region of interest 44 may be a sub-region of the internal tissue 43. In one embodiment, energy may be applied to two or more regions of interest 44 in the target tissue 43, and the total volume of the two or more regions of interest 44 may be less than about 90%, 50%, 25%, 10%, or 5% of the total volume of the tissue 43. In one embodiment, the energy is applied to only about 1%-50% of the total volume of the tissue 43, to only about 1%-25% of the total volume of the tissue 43, to only about 1%-10% of the total volume of the tissue 43, or to only about 1%-5% of the total volume of the tissue 43. In certain embodiments, only axon terminals in the region of interest 44 of the target tissue 43 would directly receive the applied energy and release neurotransmitters while the unstimulated axon terminals outside of the region of interest 44 do not receive substantial energy and, therefore, are not activated/stimulated in the same manner. In some embodiments, axon terminals in the portions of the tissue directly receiving the energy would induce an altered neurotransmitter release. In this manner, tissue subregions may be targeted for neuromodulation in a granular manner, e.g., one or more subregions may be selected. In some embodiments, the energy application parameters may be chosen to induce preferential activation of either neural or non-neuronal components within the tissue directly receiving energy to induce a desired combined physiological effect. In certain embodiments, the energy may be focused or concentrated within a volume of less than about 25 mm$^3$. In certain embodiments, the energy may be focused or concentrated within a volume of about 0.5 mm$^3$-50 mm$^3$. A focal volume and a focal depth for focusing or concentrating the energy within the region of interest 44 may be influenced by the size/configuration of the energy application device 12. The focal volume of the energy application may be defined by the field of focus or focal zone of the energy application device 12.

The energy may be substantially applied only to the region or regions of interest 44 to preferentially activate the synapse in a targeted manner to achieve targeted physiological outcomes. Accordingly, in certain embodiments, only a subset of a plurality of different types of axon terminals in the tissue 43 is exposed to the direct energy application.

Figure 4:
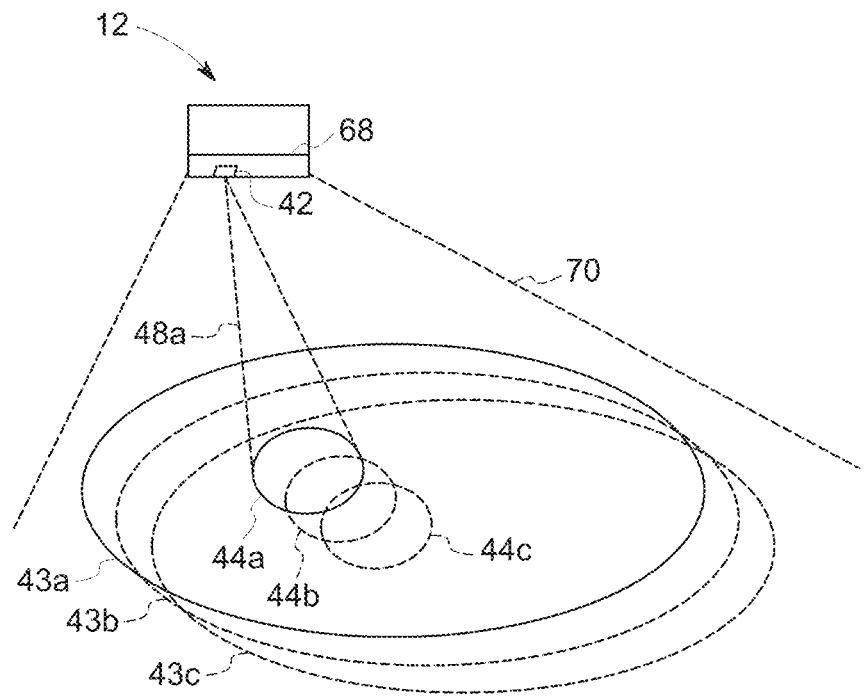
FIG. 4 is a schematic representation of an autonomous neuromodulation delivery system tracking a moving region of interest according to embodiments of the disclosure.
Figure 5:
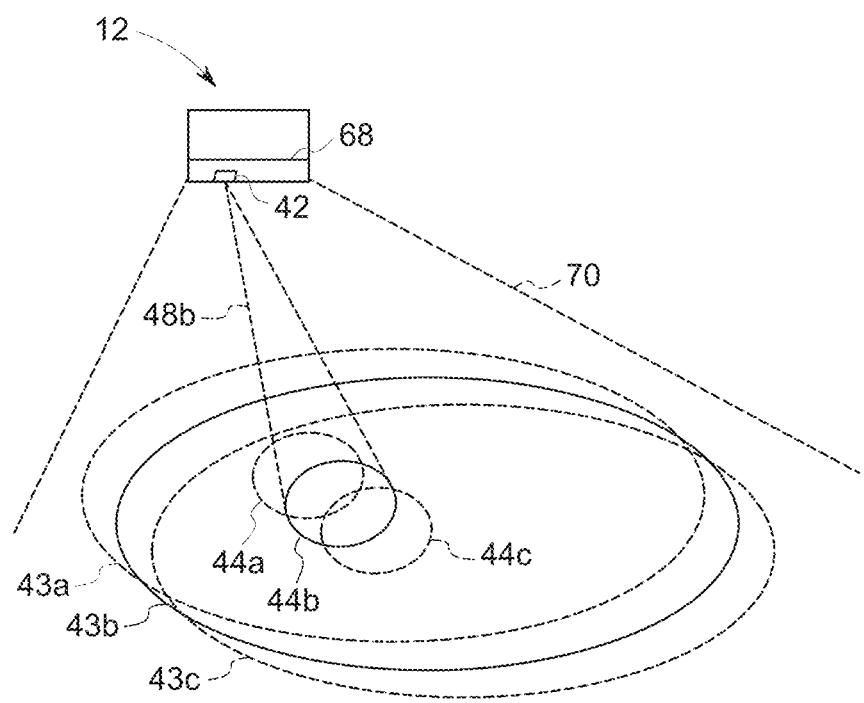
FIG. 5 is a schematic representation of adjusted energy application based on identified movement in FIG. 4.

As provided herein, identification of the correct treatment position 46 on the subject may not be sufficient to target delivery of the energy from the energy application device 12 to the region of interest 44. As depicted in FIG. 4, during treatment, the region of interest 44 may move outside of the focal zone 48 (shown as initial focal zone 48a) when the patient breathes or moves. The system 10 may be configured to acquire updated or ongoing image data of the tissue 43 (which may be acquired using timing or gating control via the controller 16 that alternates with or is acquired during dark or off periods of treatment energy delivery) using an imaging transducer 68 within the energy application device 12. The energy used to acquire the image data has different parameters than the treatment energy and may not cause the targeted physiological outcomes in one embodiment. The movement away from the transducer 42 triggers adjustment of the modulation parameters, e.g., to a higher power and/or longer time of application to achieve a desired exposure, and a steering/focusing of the ultrasound beam to a new position of the region of interest 44b, 44c, as shown in FIG. 5. Tracked movements towards the skin may result in adjustment of the modulation parameters to a lower power and/or shorter time of application as well as steering and/or focusing of the ultrasound beam to the new position.

The adjustment may be made dynamically to account for real-time movement of the region of interest 44 to achieve the desired exposure. Further, the system 10 accounts for changes to the overall modulation parameters when calculating applied energy doses. As shown, the adjustments may be made without movement of the energy application device 12 from the treatment position 46. That is, the treatment position 46 may permit energy delivery to regions of interest 44 within a potential treatment area 70, which is based on the general operating parameters and geometry of the transducer 42 and the energy application device 12. If the region of interest 44 remains within the potential treatment area 70, even while moving within the potential treatment area 70, the energy application device 12 is steered or adjusted automatically without operator intervention to permit dose delivery without interruption or physical movement of the energy application device 12 away from the treatment position 46. That is, the energy application device 12 is positioned roughly at the correct position (i.e., the treatment position 46), and fine steering/focusing is accomplished in real-time. In cases where the region of interest 44 moves outside of the zone of the potential treatment area 70, energy delivery is suspended via the controller 16. An alarm or notification may be provided. The system 10 may be configured to wait to determine (based on image data acquired from the imaging transducer 68) if the region of interest 44 returns to a position within the potential treatment area 70 before resuming. If the region of interest is not determined to be within the potential treatment area 70 after a predetermined period of time has elapsed, an indication may be provided to move the energy application device 12 to a new treatment position 46. In this manner, the energy application device is only moved upon determining that the region of interest 44 is not within the potential treatment area 70, which reduces operator burden and potential for incorrect positioning and repositioning of the energy application device 12. Further, even slightly incorrect positioning of the energy application device 12 may be corrected using the neural network or other techniques for identifying the region of interest 44 within the potential treatment zone 70.

Figure 6:
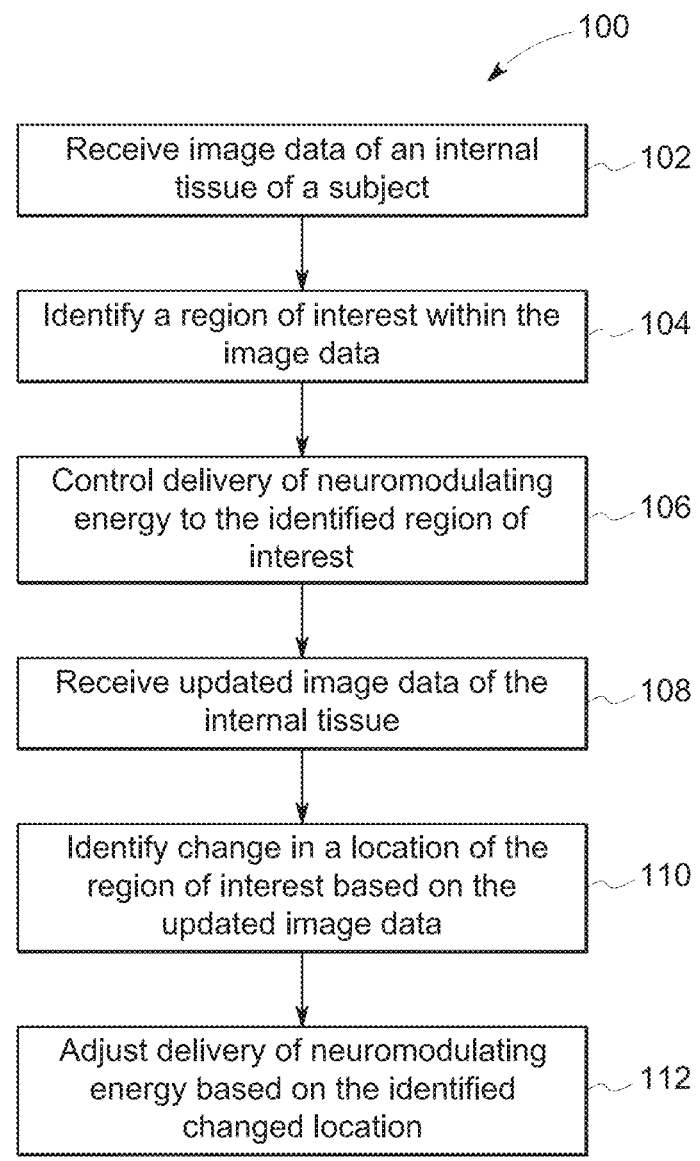
FIG. 6 is a flow diagram of an autonomous neuromodulation delivery technique according to embodiments of the disclosure.

FIG. 6 is a flow diagram of a technique 100 for neuromodulating energy delivery. Certain reference numbers discussed in conjunction with the technique 100 may be as discussed in FIGS. 1-5. The technique 100 may be performed at an initiation or establishment of a treatment protocol or as part of a verification of a treatment protocol. In certain embodiments, image data may also be part of a patient verification procedure. At step 102, image data is acquired, e.g., using the energy application device 12 in an imaging mode. The image data is provided as input to identify a region of interest 44 within the image data at step 104. Once identified, neuromodulating energy is delivered to the region of interest at step 106, e.g., by delivering energy from the energy application device that passes through the patient's skin and reaches the region of interest 44.

The system 10 may acquire updated image data at step 108 showing movement of the tissue 43 from an initial position and transitioning between various positions (see FIG. 4, tissues 43*a*, 43*b*, 43*c*) that in turn are associated with movement of the region of interest 44*b*, 44*c*. The movement or change in location is identified at step 110 and the modulation parameters of the energy application device 23 are adjusted at step 112. The system 10 may use the movement of the tissue 43 as a proxy for or estimate of the movement of the region of interest 43 in an embodiment.

In one example, the updated image data may be assessed as being characteristic of a particular type of movement. For example, a rhythmic or periodic movement of the tissue 43 and/or the region of interest towards the transducer 68 and then away from the transducer 68 that occurs over a time period (e.g., 1-5 seconds) may be characteristic of breathing. The system may predict future breaths and create a model of predicted movement of the region of interest 44 over time to align energy delivery at a particular time with a predicted position or positions of the region of interest 44 during the breath. In an additional or alternative embodiment, the system 10 may identify pauses or ends of breaths within the acquired image data and align energy delivery to time periods in which the region of interest is relatively still while the subject pauses between breaths.

In an embodiment, the system 10 may use the image data and the determined position of the region of interest 44 relative to the focal zone 48 to account for dosage delivery over time. For example, in an embodiment, the energy application device 12 may minimally adjust steering and/or focusing of energy delivery over the course of movement of the region of interest while adjusting other parameters. Based on identified movement of the region of interest 44 outside of the focal zone 48, the system 10 may calculate a total dose delivery. Accordingly, the movement may cause the system 10 to extend the period of dose delivery so that the total dose delivered directly to the region of interest 44 is within desired parameters and to account for periods when the region of interest 44 is outside of the focal zone 48 during delivery of energy. Further, the system 10 may also account for total delivery to areas outside of the region of interest 44 and adjust steering and/or focusing when energy applied outside of the region of interest 44 reaches a threshold. It should be understood that the steering may change an angle of the ultrasound beam while focusing changes the depth of focus and/or the overall size of the beam.

Figure 7:
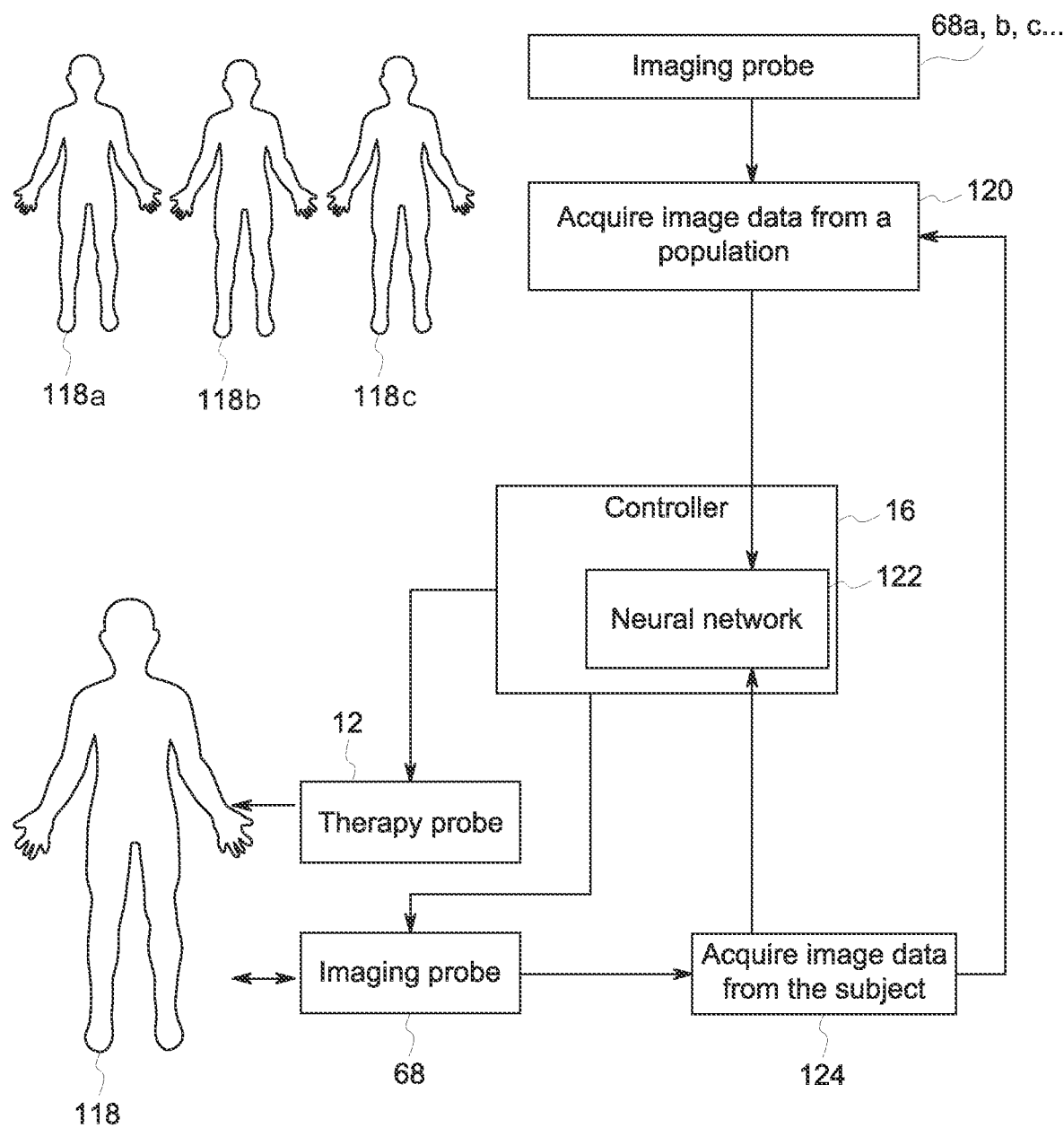
FIG. 7 is a schematic representation of inputs to a neural network according to embodiments of the disclosure.

In certain embodiments, the system 10 uses a neural network to identify a position of a region of interest 44 and/or a target tissue 43 within acquired image data. The identification may be in a generally autonomous manner with minimal operator intervention in an embodiment. FIG. 7 is a schematic representation of embodiments of building a neural network to identify a position of a region of interest 44 and/or a target tissue 43 within acquired image data. The neural network 122 may be based on image data acquired 120 from respective imaging probes 68 (e.g., 68*a*, 68*b*, 68*c*) of various subjects 118, including subjects 118*a*, 118*b*, 118*c* that are not the subject 118 of interest (i.e., receiving the dose). The neural network 122 receives the population image data and, based on certain ground truth parameters, is trained on the population image data. The neural network 122 may be specific for a particular tissue or organ and, in particular embodiments, may be specific for a particular dose regimen. As shown, the neural network 122 may be part of the controller 16. In other embodiments, the neural network 122 may be in communication with the controller 16, but not necessarily part of the controller 16. The therapy probe, which may be configured as the energy application device 12, is responsive to the controller 16 and the neural network outputs. The imaging probe 68 acquires image data from the subject 118 at step 124, and the image data is provided as an input to the neural network 122, as discussed in FIG. 8.

Figure 8:
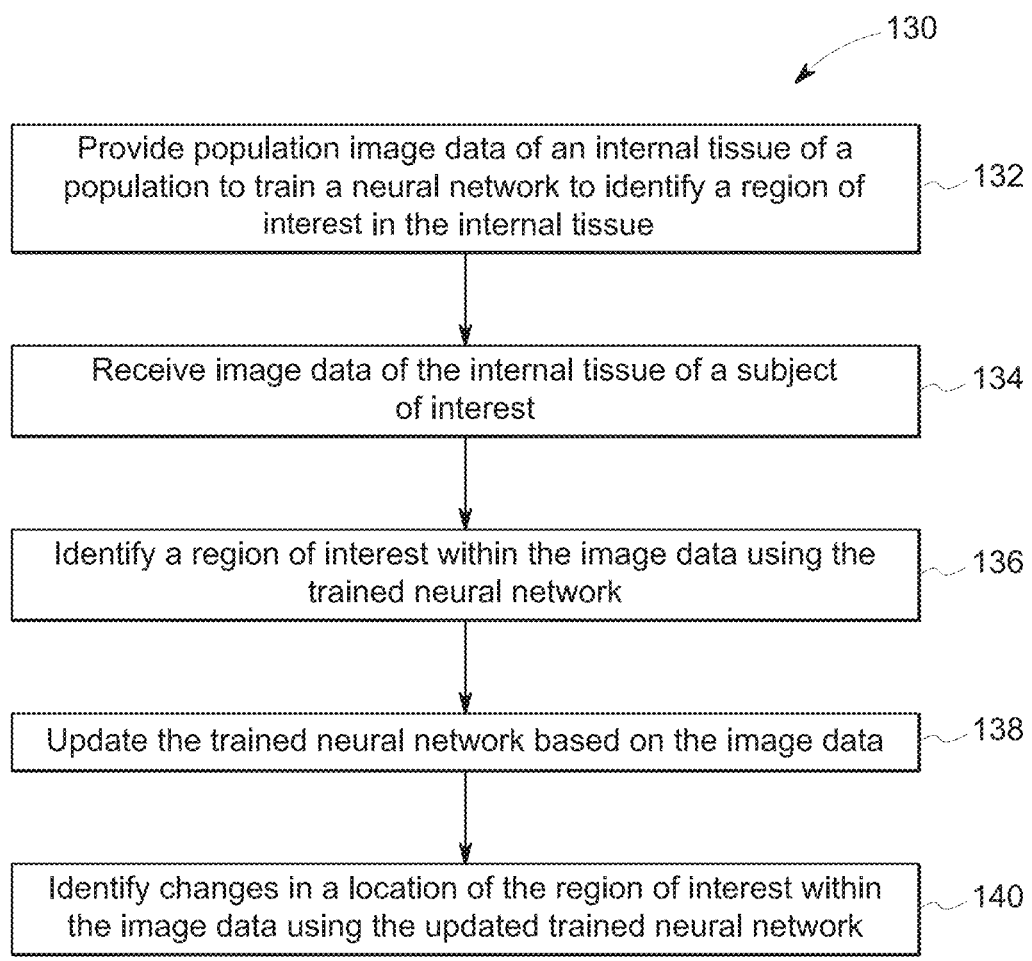
FIG. 8 is a flow diagram of an autonomous neuromodulation delivery technique according to embodiments of the disclosure.

FIG. 8 is a flow diagram of a technique 130 that may be performed in conjunction with certain elements shown in FIGS. 1-7. The technique includes the step of providing population image data to train a neural network at step 132. The technique 130 also receives image data of a subject of interest at step 134. The subject of interest may or may not be included in the population image data. Using the trained neural network, the region of interest is identified in the image data at step 136. In one embodiment, the technique 130 may include collecting images from a subject, annotating those images (for supervised learning), and the annotated images are then fed back to update the network at step 138. The updated network is then applied to all subsequent images collected from that patient. The technique 130 identifies changes in a location of the region of interest within the image data using the updated trained neural network at step 140

Further, the technique 130 may include selecting a subset of all collected images from the patient to annotate and use for network update because data annotation can a laborious process. The images of the subset to be used for network update may be selected based on a variety of factors, one of them being how well the existing population based model of the network performs on that image. For example, if the population-based model already performs well on a given image, there may be little benefit to updating the model with that image. However, for images where the network provides poor results, which may be either manually detected or have other criteria to be automatically detected (such as low probability scores etc.), expert annotations may be obtained for such an image and then provided to the network.

As discussed herein, the neural network 122 may include one or more layers that permit identification of organs and/or structures. Certain layers of the neural network 122 may be suspended or frozen while other layers of the network are trained with data from the subject of interest to tailor the model to a particular individual. While large, deep networks are powerful, such networks operate on large amounts of data. Where there is a limited amount of data, as is likely to be the case for an individual subject, certain layers from the population-based model may be frozen to reduce the number of parameters that the network has to learn. Since the population-based model has also been trained on the same type of images and/or for the same type of task, the weights and filters it has learned in layers closer to the input layer is usually sufficiently low-level (i.e. edges, lines etc.) that re-learning provides limited benefit. The neural network may be a supervised or unsupervised neural network. The neural network 122 may be updated to accommodate patient-specific changes in a subject. Further, the neural network 122 may include a verification step to assess a confidence of recognizing a region of interest (see FIG. 15). In an embodiment, the patient-specific model may be validated on an independent dataset from that patient to ensure that the overall accuracy of the model has improved for the patient in question before deployment on their therapeutic device.

Figure 9:
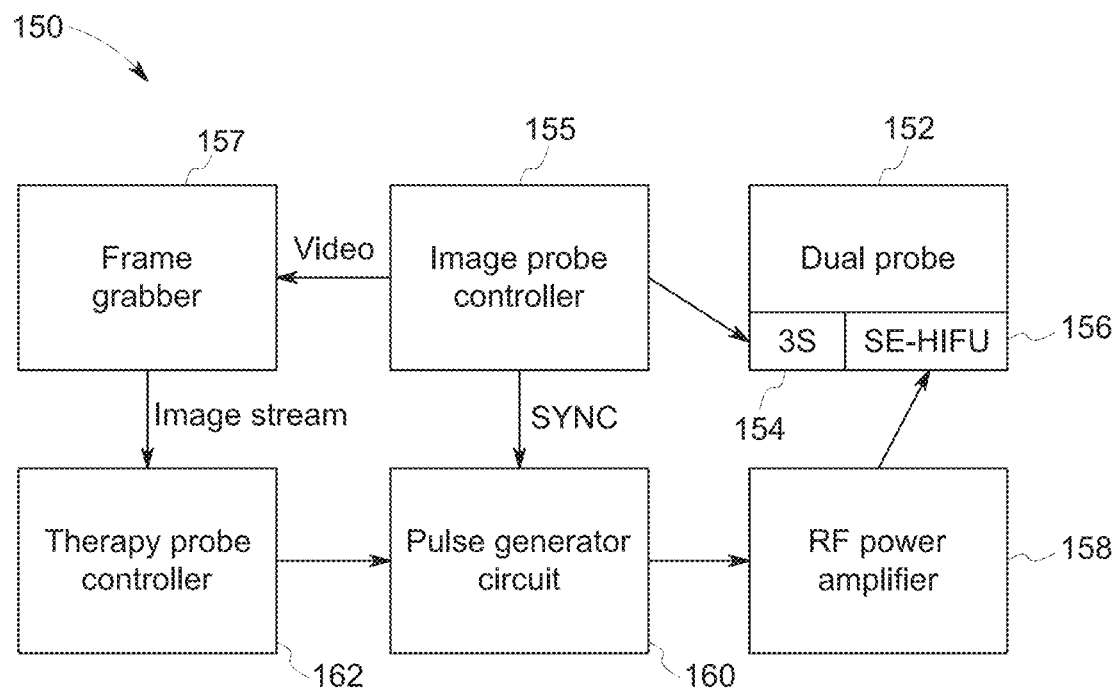
FIG. 9 is a block diagram of an example of an autonomous neuromodulation delivery system including a dual imaging and therapy probe according to embodiments of the disclosure.
Figure 10:
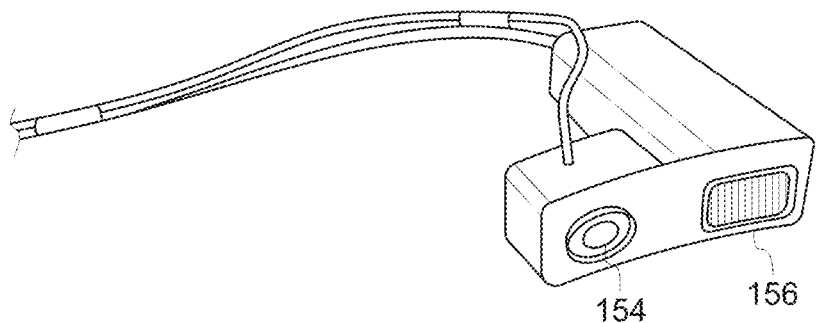
FIG. 10 is an image of the dual imaging and therapy probe of FIG. 9.

FIG. 9 is an example system 150 that may be used in conjunction with or as part of the system 10. The system 150 includes various features to permit image acquisition, such as a dual function probe 152 (see FIG. 10) that includes an imaging transducer 156, shown as a GE 3S Sector Array Probe (General Electric) and a therapy probe 154, shown as a high intensity focused ultrasound (HIFU) probe, as well as an image probe controller 155 that controls image acquisition via the imaging transducer 156. The system 150 also includes a frame grabber 157 that operates on the acquired image data. It should be understood that, while certain embodiments operate on rendered images from acquired image data, the system 10 may also use raw or unrendered image data as an input. The therapy probe 154 may operate under control of a therapy probe controller 162 that controls a pulse generator circuit 160 and an RF power amplifier 158.

FIG. 11 shows an example of a graphical user interface that may be used in conjunction with the system 10 and that shows images acquired using the system 150. The graphical user interface shows the neuromodulation prescription, which may refer to a treatment protocol (including treatment dates or timing information for an individual subject) and/or target tissue and may in certain embodiments include a total energy of individual doses as well as associated observable parameters associated with treatment. For example, the prescription may set forth goals for changes in concentrations of molecules of interest relative to a baseline before a start of treatment. The user interface may indicate treatment status as well as an acquired ultrasound image, e.g., the acquired image data of the subject, and the neural network-provided caption indicating the anatomy detected in the image. The neural network identified a kidney anatomical structure. However, the associated treatment protocol is for delivery of autonomous neuromodulating energy to the liver.

Figure 12:
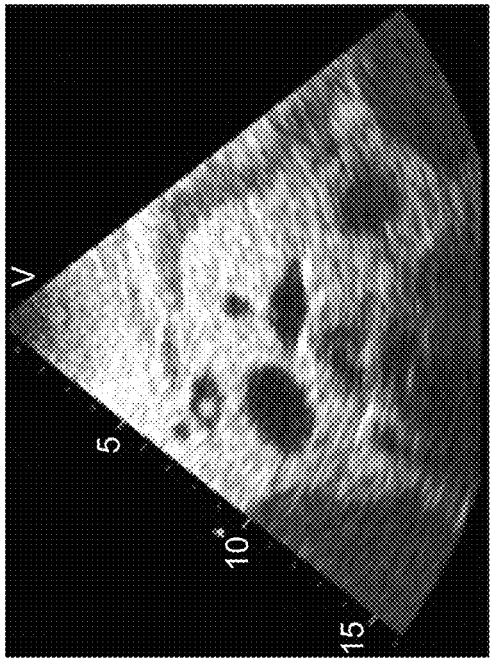
FIG. 12 is an example graphical user interface of an autonomous neuromodulation delivery system during an alignment with a region of interest according to embodiments of the disclosure.
Figure 13:
FIG. 13 is an example graphical user interface of an autonomous neuromodulation delivery system during delivery of neuromodulating energy to the region of interest according to embodiments of the disclosure.

Accordingly, as shown in the example graphical user interface of FIG. 12, upon starting the dose, the system waits for the target anatomy (in this case liver) to appear in the field of view before delivering the therapy. The identified probe placement is not suited for delivering the therapy and therefore the status indicates "aligning." In FIG. 13, the therapy or neuromodulating energy dose is delivered upon determination that the anatomy of interest aligns with the anatomy in the field of view as identified by the neural network. The status indicates "delivering," and the therapy beam is visualized in the ultrasound image. In FIG. 14, the system stops delivering the therapy even when focused on the target organ (i.e., the liver), and the total energy of the individual dose is complete as shown in this frame.

Figure 15:
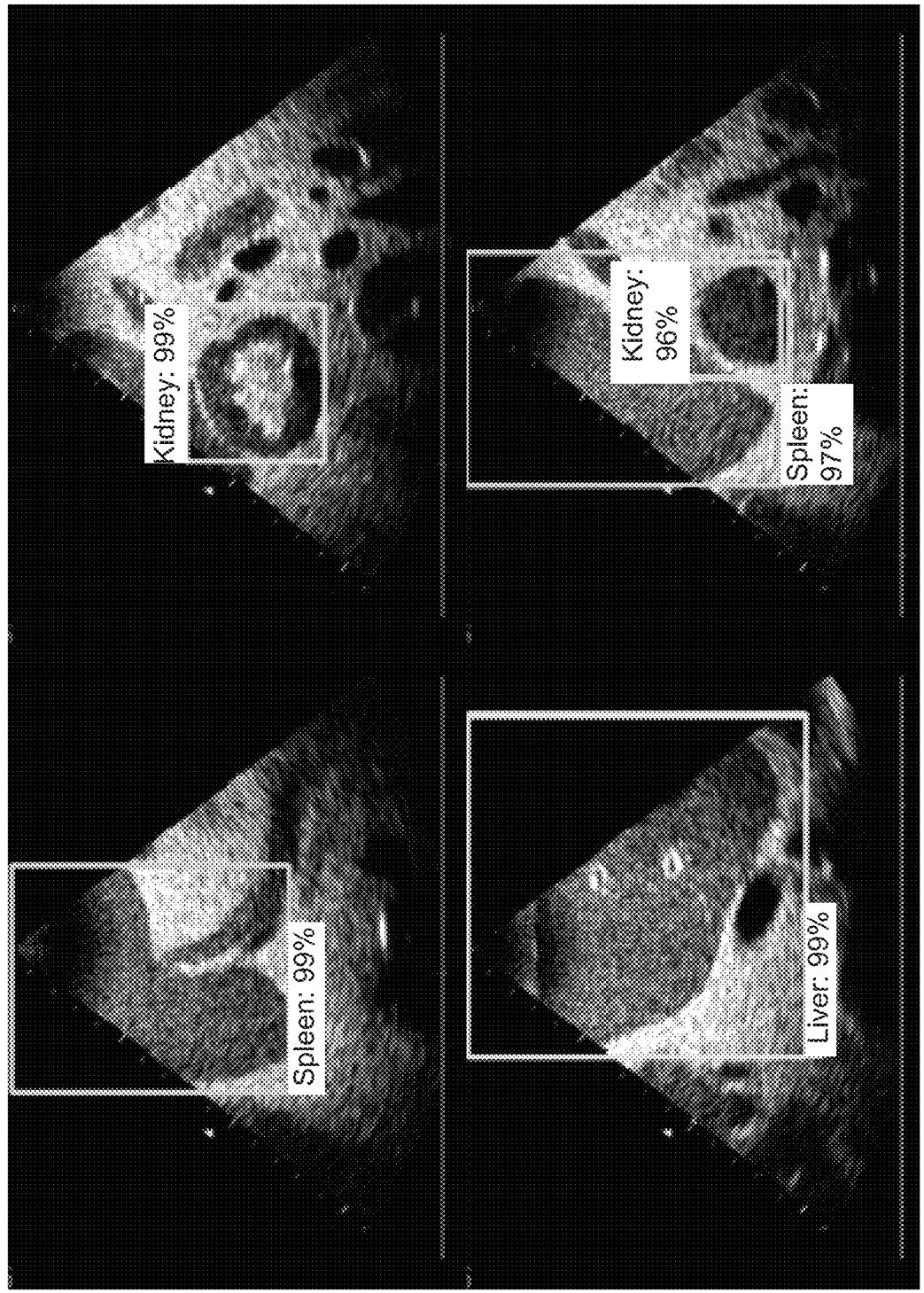
FIG. 15 shows examples of organ identification using the autonomous neuromodulation delivery system according to embodiments of the disclosure.

FIG. 15 shows results from a neural network trained for organ detection that identifies and localizes spleen, kidney and liver on ultrasound images. The captured images include probabilistic indications of identification (e.g., 99%, 97%). In an embodiment, the identification of the organ or region of interest within the organ may be based on reaching a probabilistic threshold of identification based on the output of the neural network. In one example, the threshold may be at least 95%, at least 97%, or at least 99%.

The disclosed techniques permit delivery of neuromodulating energy that accounts for movement of a desired region of interest. The movement may be movement during a treatment, e.g., as a result of breathing or blood flow. The movement may also be a repositioning or change in organ size between spaced apart doses. For example, patient weight loss or clinical condition may change a size or depth of an organ. In turn, these changes may be assessed to provide more accurate neuromodulating energy delivery.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of delivery of neuromodulating energy, the method comprising:
   receiving image data of a subject;
   operating a neural network trained on images from a population of subjects to provide a determination that the received image data aligns with a region of interest, wherein providing the determination comprises:
      generating a probabilistic indication of identification based on output from the neural network;
      comparing the probabilistic indication of identification to a probabilistic threshold of identification; and
      returning a signal indicative of identification and alignment upon determining that the probabilistic indication of identification is at or above the probabilistic threshold of identification;
   controlling a pulse generator to deliver energy to the region of interest responsive to the returned signal being indicative of identification and alignment, wherein the energy is a portion of a total energy of an individual dose to be delivered to the region of interest and wherein the energy is delivered using an energy application device;
   acquiring updated image data from the subject while delivering the energy and before the total energy of the individual dose is delivered, the updated image data being representative of an internal tissue comprising the region of interest;
   identifying a change in location of the region of interest relative to the energy application device based on the updated image data using the neural network; and
   suspending energy delivery responsive to the signal not being returned from the neural network based on providing a determination that the updated image data does not align with the region of interest.

2. The method of claim 1, comprising: acquiring the image data using the energy application device.

3. The method of claim 1, comprising: acquiring additional image data and delivering additional energy while the returned signal being indicative of identification and alignment and until the total energy of the individual dose is applied to the region of interest.

4. The method of claim 3, comprising reducing a power of the additional energy based on the region of interest moving closer to the energy application device or increasing the power of the additional energy based on the region of interest moving further from the energy application device.

5. The method of claim 3, comprising changing a focus location of an ultrasound beam via steering, focusing to deliver the additional energy based on the change in location of the region of interest, or both.

6. A neuromodulation system, comprising:
a pulse generator;
an ultrasound energy application device configured to receive energy pulses from the pulse generator and to deliver a neuromodulating energy dose to a region of interest in a subject; and
a controller in communication with the pulse generator, the controller configured to:
  receive image data, the image data being representative of an internal tissue of the subject;
  operate a neural network that has been trained on images of respective internal tissues of a population of subjects to provide a determination that the received image data aligns with the region of interest, wherein the determination comprises:
    generating a probabilistic indication of identification based on output from the neural network;
    comparing the probabilistic indication of identification to a probabilistic threshold of identification; and
    returning a signal indicative of identification and alignment upon determining that the probabilistic indication of identification is at or above the probabilistic threshold of identification;
  control the pulse generator to initiate application of the neuromodulating energy dose via the ultrasound energy application device to the region of interest based on the returned signal being indicative of identification and alignment;
  receive updated image data while delivering the neuromodulating energy dose;
  identify a change in location of the region of interest relative to the energy application device based on the updated image data using the neural network; and
  suspend energy delivery responsive to the signal not being returned from the neural network based on providing a determination that the updated image data does not align with the region of interest.

7. The system of claim 6, wherein the controller is configured to predict a movement path of the region of interest using the neural network and to dynamically change the one or more control parameters based on the movement path that is predicted.

8. The system of claim 6, wherein the neural network is trained to identify the region of interest comprising a porta hepatis in a liver.

9. The system of claim 6, wherein the neural network is trained to characterize the change in location of the region of interest that is characteristic of a breathing pattern of the subject based on the updated image data and to adjust the application of the neuromodulating energy to periods predicted to be between breaths of the subject.

10. The system of claim 6, wherein the energy application device is controlled such that the neuromodulating energy is not applied to areas outside of the region of interest.

11. The system of claim 6, wherein the controller is configured to use the neural network to track movement of the region of interest and to automatically steer the energy application device based on the tracked movement.

12. The system of claim 11, wherein the automatic steering comprises reducing a power of the energy pulses based on the region of interest moving closer to the energy application device or increasing the power of the energy pulses based on the region of interest moving further from the energy application device.

13. The system of claim 6, wherein the controller is configured to automatically control the energy application device to steer and/or focus an ultrasound beam formed by the ultrasound energy application device to the region of interest that is identified by the neural network.

14. The system of claim 6, wherein the ultrasound energy application device comprises a motor configured to change a position or angle of the ultrasound energy application device and/or a transducer of the energy application device relative to the subject in response to instructions from the controller to align a beam of the neuromodulating energy with the region of interest.

15. The system of claim 6, comprising an imaging transducer configured to acquire the image data and the updated image data.

16. The system of claim 15, wherein the imaging transducer is part of the ultrasound energy application device such that the imaging transducer is in contact with the subject during the application of the neuromodulating energy.

17. The system of claim 6, wherein the neural network is updated using the image data, the updated image data, or both from the subject.

18. The system of claim 6, wherein the region of interest is defined by a presence of specific anatomical structures in the subject.

19. The system of claim 18, wherein the anatomical structures include one or more of organs, nerves, nerve plexus, and vessels, and wherein the neural network is trained on identifying the anatomical structures within or neighboring in the region of interest.

20. The system of claim 18, wherein the anatomical structure is within a liver or a spleen.

21. The system of claim 18, wherein the neural network comprises one or more layers configured to identify the anatomical structures.

* * * * *